United States Patent [19]

Oppenheim et al.

[11] Patent Number: 5,726,039
[45] Date of Patent: Mar. 10, 1998

[54] VECTORS AND TRANSFORMED HOST CELLS FOR RECOMBINANT PROTEIN PRODUCTION AT REDUCED TEMPERATURES

[75] Inventors: Amos B. Oppenheim, Jerusalem; Hilla Giladi, Mevasseret Zion; Daniel Goldenberg, Ma'ale Adumimn; Simi Kobi, Jerusalem; Idit Azar, Rehovot, all of Israel

[73] Assignee: Yissum Research Development Co. of The Hebrew University of Jerusalem, Jerusalem, Israel

[21] Appl. No.: 504,718

[22] Filed: Jul. 20, 1995

Related U.S. Application Data

[63] Continuation-in-part of Ser. No. 278,281, Jul. 21, 1994, Pat. No. 5,654,169.
[51] Int. Cl.$^6$ ............ C12P 21/02; C12N 15/20; C12N 15/73; C07H 21/04
[52] U.S. Cl. .............. 435/69.1; 435/320.1; 536/24.1
[58] Field of Search .................. 435/69.1, 320.1; 536/24.1

[56] References Cited

PUBLICATIONS

Giladi et al. Supercoiling, integration host factor, and a dual promoter system, participate in the control of the bacteriophage lambda pL promoter J. Mol. Biol. vol. 224 937–948, (1992).

Giladi et al. Enhanced activity of the bacteriophage lambda pL promoter at low temperature Proc. Natl. Acad. Sci. U.S.A. vol. 92 2184–2188, (1995).

Lee et al. Family of the major cold–shock protein, CspA)CS7.4), of *Escherichia coli*, whose members show a high sequence similarity withthe eukaryotic y–box binding proteins Mol. Mocrobiol. vol. 11 833–839, (1994).

Shirano et al. Low temperature cultivation of *Escherichia coli* carrying a rice lipoxygenase L–2 cDNA produces a soluble and active enzyme at a high level FEBS Lett. vol. 271 128–130, (1990).

Tanabe et al. Identification of the promoter region of the *Escherichia coli* major cold shock gene, cspA J. Bacteriol. vol. 174 3867–3873, (1992).

Kulakauskas et al. Efficient introduction of cloned mutant alleles into the *Escherichia coli* chromosome J. Bacteriol. vol. 173 2633–2638, (1991).

Horne et al. The leftward promoter of bacteriophage lambda J. Biol. Chem. vol. 256 2003–2009, (1981).

*Primary Examiner*—Nancy Degen
*Assistant Examiner*—John S. Brusca
*Attorney, Agent, or Firm*—Oblon, Spivak, McClelland, Maier & Neustadt, P.C.

[57] ABSTRACT

The invention relates to an expression vector, the nucleic acid sequence of which comprises a promoter that is capable of controlling, when the vector is in a bacterial host and the temperature is lowered to below about 20° C., the production of recombinant peptide or protein encoded by a gene contained within the vector. The invention also relates to host cells containing the vectors and to a method of producing a recombinant protein.

26 Claims, 19 Drawing Sheets pL DNA

EcoRI
GGCCTCAGCGCCGGGTTTTCTTTGCCTCACGATCGCCCCCAAAAACACATAACCAATTGTATTTATTGAAAAA
CCGGAGTCGCGGCCCAAAAGAAACGGAGTGCTAGCGGGGGGTTTTTGTGTATTGGTTAACATAAATAACTTTTT
                                    L2

TAAATAGATACAACTCACTAAACATAGCCAATTCAGATCTCTCACCTACCAAACAATGCCCCCCTGCAAAAA
ATTTATCTATGTTGAGTGATTTGTATCGTTAAGTCTAGAGAGTGGATGGTTTGTTACGGGGGGACGTTTTT
                    BglII                                      pL2
                                                                 →
                               (-50)      ┌─────────────────────────────┐
                               GGCC    AAA┤TTATCTCTGGGGTGT├TGACATAAA┤TA│
                         A  ┌──GACCATCTGGGTGATA├──────────┤          │  │
TAAATTCATATAAAAACATACAGA├──┤          ├─────────────────────────────┘  │
├───────────────────────┘   │-35       │                  -35           │
         L1                 └──────────┘                                │
                                                       (sex1)           │
                                                         T              │
                                                         -35            │

FIG. 1A

```
181  GACAGGATTAAAAATCGATGATTTCGCCCGGGTTTTGGGCGTATCAGTCGCCATGGTAAA  240
     CTGTCCTAATTTTTAGCTACTAAAGCGGGCCCAAAACCCGCATAGTCAGCGGTACCATTT
          EL
           →
241  GGAATGGGAATCCAGACGCGTGAAGCCTTCAAGTGCCGAACTAAAAATTGATGCGTTTGAT  300
     CCTTACCCTTAGGTCTGCGCACTTCGGAAGTTCACGGCTTGATTTTAACTACGCAAACTA

301  TCAAGCCAACCCGGCATTAAGTAAGCAGTTGATGGAATAGACTTTTATCCACTTTATTGC  360
     AGTTCGGTTGGGCCGTAATTCATTCGTCAACTACCTTATCTGAAAATAGGTGAAATAACG

361  TGTTTACGGTCCTGATGACAGGACCGTTTTCCAACCGATTAATCATAAATATGAAAAATA  420
     ACAAATGCCAGGACTACTGTCCTGGCAAAAGGTTGGCTAATTAGTATTTATACTTTTTAT
```

FIG. 7A

```
      PcspA
         -35                                  -10        +1
     ATTGTTGCATCACCCGCCAATGCGTGGCTTAATGCACATCAACGGTTTGACGTACAGACC
421  ------------------------------+-----------------------------  480
     TAACAACGTAGTGGGCGGTTACGCACCGAATTACGTGTAGTTGCCAAACTGCATGTCTGG ATTAAAGCAGTGTAGTAAGGCAAGTCCCCTTCAAGAGTTATCGTTGATACCCCTCGTAGTG
481  ------------------------------+-----------------------------  540
     TAATTTCGTCACATCATTCCGTTCAGGGAAGTTCTCAATAGCAACTATGGGAGCATCAC CACATTCCTTTAACGCTTCAAAATCTGTAAAGCACGCCATATCGCCGAAAGGCACACTTA
541  ------------------------------+-----------------------------  600
     GTGTAAGGAAATTGCGAAGTTTTAGACATTTCGTGCGGTATAGCGGCTTTCCGTGTGAAT
                        ↓ EL
```

FIG. 7B

```
181  GACAGGATTAAAAAATCGATGATTTCGCCCGGGTTTTGGGCGTATCAGTCGCCATGGTAAA   240
     CTGTCCTAATTTTTTAGCTACTAAAGCGGGCCCAAAACCGCATAGTCCCCGGTACCATTT

241  GGAATGGGAATCCAGACGCGTGAAGCCTTCAAGTGCCGAACTAAAATTGATGCGTTTGAT   300
     CCTTACCCTTAGGTCTGCGCACTTCGGAAGTTCACGGCTTGATTTTAACTACGCAAACTA

L
                                            →
301  TCAAGCCAACCCGGCATTAAGTAGTAAGCAGTTGATGGAATAGACTTTTATCCACTTTATTGC   360
     AGTTCGGTTGGGCCGTAATTCATTCGTCAACTACCCTTATCTGAAAATAGGTGAAATAACG
```

*FIG. 9A*

```
                                                                                    420
361  TGTTTACGGTCCTGATGACAGGACCGTTTCCAACCGATTAATCATAAATATGAAAAATA
     ACAAATGCCAGGACTACTGTCCTGGCAAAAGGTTGGCTAATTAGTATTATACTTTTTAT
              -35                                        -10        +1
                                                                                    480
421  ATTGTTGCATCACCCGCCAATGCGTTGGCTTTAATGCACATCAAGCGGTTTGACGTACAGACC
     TAACAACGTAGTGGGCGGTTACGCAACCGAATTACGTGTAGTTGCCAAACTGCATGTCTGG
                                                                                    540
481  ATTAAAGCAGTGTAGTAAGGCAAGTCCCCTTCAAGAGTTATCGTTGATACCCCTCGTAGTG
     TAATTTCGTCACATCATTCCGTTCAGGGAAGTTCTCAATAGCAACTATGGGAGCATCAC
                                                                                    600
541  CACATTCCTTTAACGCTTCAAAATCTGTAAAGCACGCCATATCGCCGAAAGGCACACTTA
     GTGTAAGGAAATTGCGAAGTTTTAGACATTTCGTGCGGTATAGCGGCTTTCCGTGTGAAT
                              ↓
                              L
```

*FIG. 9B*

```
181  GACAGGATTAAAAATCGATGATTTCGCCCGGGTTTTGGGCGTATCAGTCGCCATGGTAAA  240
     CTGTCCTAATTTTTAGCTACTAAAGCGGGCCCAAAACCCGCATAGTCAGCGGTACCATTT

241  GGAATGGGAATCCAGAGACGCGTGAAGCCTTCAAGTGCCGAACTAAAATTGATGCGTTTGAT  300
     CCTTACCCTTAGGTCTGCGCACTTCGGAAGTTCACGGCTTGATTTTAACTACGCAAACTA

301  TCAAGCCAACCCCGGCATTAAGTAAGCAGTTGATGGAATAGACTTTTATCCACTTTATTGC  360
     AGTTCGGTTGGGCCGTAATTCATTCGTCAACTACCCTTATCTGAAAATAGGTGAAATAACG
                                                    M
                                                    →

361  TGTTTACGGTCCTGATGACAGGACCGTTTTCCAACCGATTAATCATAAATATGAAAAATA  420
     ACAAATGCCAGGACTACTGTCCTGGCAAAAGGTTGGCTAATTAGTATTTATACTTTTTAT
```

*FIG. 11A*

```
181  GACAGGATTAAAAATCGATGATTTCGCCCGGGTTTTGGGCGTATCAGTCGCCATGGTAAA  240
     CTGTCCTAATTTTTAGCTACTAAAGCGGGCCCAAACCCGCATAGTCAGCGGTACCATTT

241  GGAATGGGAATCCAGACGCGTGAAGCCTTCAAGTGCCGAACTAAAATTGATGCGTTTGAT  300
     CCTTACCCTTAGGTCTGCGCACTTCGGAAGTTCACGGCTTGATTTTAACTACGCAAACTA

301  TCAAGCCAACCCGGCATTAAGTAAGCAGTTGATGGAATAGACTTTTATCCACTTTATTGC  360
     AGTTCGGTTGGGCCGTAATTCATTCGTCAACTACCCTTATCTGAAAATAGGTGAAATAACG

361  TGTTTACGGTCCTGATGACAGGACCGTTTCCAACCGATTAATCATAAATATGAAAAATA  420
     ACAAATGCCAGGACTACTGTCCTGGCAAAAGGTTGGCTAATTAGTATTTATACTTTTTAT
```

*FIG. 13A*

```
                                                            +1
       -35                       -10                        →
     ATTGTTGCATCACCCGCCAATGCGTTGGCTTAATGCACATCAACGGGTTTGACGTACAGACC
421  ----------+---------+---------+---------+---------+---------+ 480
     TAACAACGTAGTGGGCGGTTACGCAACCGAATTACGTGTAGTTGCCAAACTGCATGTCTGG

ATTAAAGCAGTGTAGTAAGGCAAGTCCCTTCAAGAGTTATCGTTGATACCCCTCGTAGTG
481  ----------+---------+---------+---------+---------+---------+ 540
     TAATTTCGTCACATCATTCCGTTCAGGGAAGTTCTCAATAGCAACTATGGGAGCATCAC

CACATTCCTTTAACGCTTCAAAATCTGTAAAGCACGCCATATCGCCGAAAGGCACACTTA
541  ----------+---------+---------+---------+---------+---------+ 600
     GTGTAAGGAAATTGCGAAGTTTTAGACATTTCGTCCGGTATAGCGGCTTTCCGTGTGAAT
                      ↓
                      S
```

*FIG. 13B*

FIG. 18
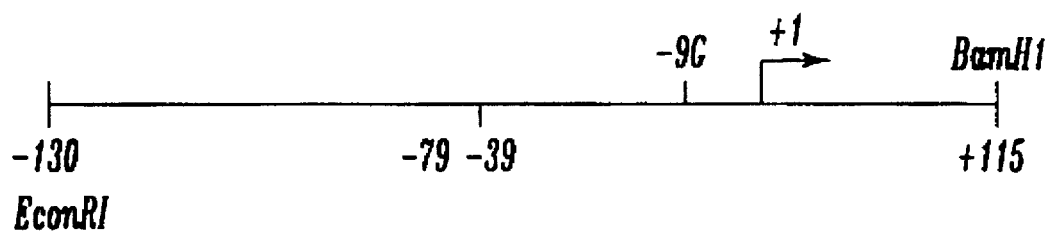
PLASMID pH309
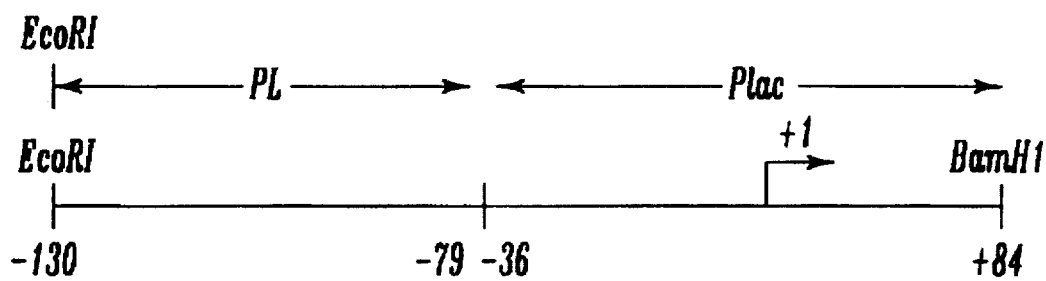
PLASMID pL-plac

FIG. 19

| PROMOTER FRAGMENT | β-GALACTOSIDASE UNITS OVERNIGHT INCUBATION | | | TEMPORL COLD SHOCK | | | mRNA level |
|---|---|---|---|---|---|---|---|
| | 37°C | 15°C | | 37°C | 15°C | | 15°C/37°C |
| PcspA → lacZ  −449 / +1 / +81 | 5,950 | 35,730 | (6.0) | 3,620 | 8,890 | (2.45) | 2.8 |
| PcspA → lacZ  −209 / +1 / +81 | 5,500 | 31,860 | (5.6) | 3,820 | 9,460 | (2.5) | 4.2 |
| PcspA → lacZ  −59 / +1 / +81 | 2,970 | 28,170 | (9.5) | 2,240 | 8,990 | (4.0) | 2.5 |
| PcspA → lacZ  −40 / +1 / +81 | 1,080 | 11,500 | (10.6) | 920 | 3,640 | (4.0) | 4.0 |
| PcspA → lacZ  −40 / +1 / +16 | 4,180 | 17,030 | (4.1) | 1,840 | 4,920 | (2.7) | 3.2 |
| PcspA → lacZ  −37 / +1 / +3 | 10,870 | 11,140 | (1.03) | 4,670 | 5,190 | (1.0) | 1.0 |
| P*cspA → lacZ  −209 / +1 / +81 | 2,260 | 47,520 | (21) | 2,040 | 14,880 | (7.3) | 10.0 |

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 343 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
CGGGTTTTCT  TTGCCTCACG  ATCGCCCCCA  AAACACATAA  CCAATTGTAT  TTATTGAAAA    60
ATAAATAGAT  ACAACTCACT  AAACATAGCA  ATTCAGATCT  CTCACCTACC  AAACAATGCC   120
CCCCTGCAAA  AAATAAATTC  ATATAAAAAA  CATACAGATA  ACCATCTGCG  GTGATAAATT   180
ATCTCTGGCG  GTGTTGACAT  AAATACCACT  GGCGGTGATA  CTGAGCACAT  CAGCAGGACG   240
CACTGACCAC  CATGAAGGTG  ACGCTCTTAA  AAATTAAGCC  CTGAAGAAGG  GCAGCATTCA   300
AAGCAGAAGG  CTTTGGGGTG  TGTGATACGA  AACGAAGCAT  TGG                      343
```

( 2 ) INFORMATION FOR SEQ ID NO:2:

( i ) SEQUENCE CHARACTERISTICS:
        ( A ) LENGTH: 343 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CGGGTTTTCT  TTGCCTCACG  ATCGCCCCCA  AAACACATAA  CCAATTGTAT  TTATTGAAAA    60
ATAAATAGAT  ACAACTCACT  AAACATAGCA  ATTCAGATCT  CTCACCTACC  AAACAATGCC   120
CCCCTGCAAA  AAATAAATTC  ATATAAAAAA  CATACAGATA  ACCATCTGCG  GTGATAGGCC   180
ATCTCTGGCG  GTGTTGACAT  AAATACCACT  GGCGGTGATG  CTGAGCACAT  CAGCAGGACG   240
CACTGACCAC  CATGAAGGTG  ACGCTCTTAA  AAATTAAGCC  CTGAAGAAGG  GCAGCATTCA   300
AAGCAGAAGG  CTTTGGGGTG  TGTGATACGA  AACGAAGCAT  TGG                      343
```

( 2 ) INFORMATION FOR SEQ ID NO:3:

( i ) SEQUENCE CHARACTERISTICS:
        ( A ) LENGTH: 290 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PROMOTER"

( x i ) SEQUENCE DESCRIPTION: SEQ ID NO:3:

```
CAGACGCGTG  AAGCCTTCAA  GTGCCGAACT  AAAATTGATG  CGTTTGATTC  AAGCCAACCC    60
GGCATTAAGT  AAGCAGTTGA  TGGAATAGAC  TTTATCCAC   TTTATTGCTG  TTTACGGTCC   120
```

```
TGATGACAGG  ACCGTTTTCC  AACCGATTAA  TCATAAATAT  GAAAAATAAT  TGTTGCATCA    180

CCCGCCAATG  CGTGGCTTAA  TGCACATCAA  CGGTTTGACG  TACAGACCAT  TAAAGCAGTG    240

TAGTAAGGCA  AGTCCCTTCA  AGAGTTATCG  TTGATACCCC  TCGTAGTGCA                290
```

( 2 ) INFORMATION FOR SEQ ID NO:4:

( i ) SEQUENCE CHARACTERISTICS:
        ( A ) LENGTH: 191 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PROMOTER"

( x i ) SEQUENCE DESCRIPTION: SEQ ID NO:4:

```
CTTTATTGCT  GTTTACGGTC  CTGATGACAG  GACCGTTTTC  CAACCGATTA  ATCATAAATA    60

TGAAAAATAA  TTGTTGCATC  ACCCGCCAAT  GCGTGGCTTA  ATGCACATCA  ACGGTTTGAC    120

GTACAGACCA  TTAAAGCAGT  GTAGTAAGGC  AAGTCCCTTC  AAGAGTTATC  GTTGATACCC    180

CTCGTAGTGC  A                                                              191
```

( 2 ) INFORMATION FOR SEQ ID NO:5:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PROMOTER"

( x i ) SEQUENCE DESCRIPTION: SEQ ID NO:5:

```
TCATAAATAT  GAAAAATAAT  TGTTGCATCA  CCCGCCAATG  CGTGGCTTAA  TGCACATCAA    60

CGGTTTGACG  TACAGACCAT  TAAAGCAGTG  TAGTAAGGCA  AGTCCCTTCA  AGAGTTATCG    120

TTGATACCCC  TCGTAGTGCA                                                     140
```

( 2 ) INFORMATION FOR SEQ ID NO:6:

( i ) SEQUENCE CHARACTERISTICS:
        ( A ) LENGTH: 121 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PROMOTER"

( x i ) SEQUENCE DESCRIPTION: SEQ ID NO:6:

```
TTGTTGCATC  ACCCGCCAAT  GCGTGGCTTA  ATGCACATCA  ACGGTTTGAC  GTACAGACCA    60

TTAAAGCAGT  GTAGTAAGGC  AAGTCCCTTC  AAGAGTTATC  GTTGATACCC  CTCGTAGTGC    120

A                                                                          121
```

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:7:

AAGAATTCGG GTTTTCTTT                                                           19

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:8:

AAGAGCGTCA CCTTC                                                               15

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:9:

TCAGAATTCT CACCTACC                                                            18

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:10:

TATGTCAACA CCTTTTTAT ATG                                                       23

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:11:

AAGGATCCAA TGCTTCGTTT                                                          20

( 2 ) INFORMATION FOR SEQ ID NO:12:

( i ) SEQUENCE CHARACTERISTICS:
        ( A ) LENGTH: 356 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| GGCCTCAGCG | CCGGGTTTTC | TTTGCCTCAC | GATCGCCCCC | AAAACACATA | ACCAATTGTA | 60
| TTTATTGAAA | AATAAATAGA | TACAACTCAC | TAAACATAGC | AATTCAGATC | TCTCACCTAC | 120
| CAAACAATGC | CCCCCTGCAA | AAAATAAATT | CATATAAAAA | ACATACAGAT | GACCATCTGC | 180
| GGTGATAAAT | TATCTCTGGC | GGTGTTGACA | TAAATACCAC | TGGCGGTGAT | ACTGAGCACA | 240
| TCAGCAGGAC | GCACTGACCA | CCATGAAGGT | GACGCTCTTA | AAAATTAAGC | CCTGAAGAAG | 300
| GGCAGCATTC | AAAGCAGAAG | GCTTTGGGGT | GTGTGATACG | AAACGAAGCA | TTGGCC | 356

( 2 ) INFORMATION FOR SEQ ID NO:13:

( i ) SEQUENCE CHARACTERISTICS:
        ( A ) LENGTH: 420 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| GACAGGATTA | AAAATCGATG | ATTTCGCCCG | GGTTTTGGGC | GTATCAGTCG | CCATGGTAAA | 60
| GGAATGGGAA | TCCAGACGCG | TGAAGCCTTC | AAGTGCCGAA | CTAAAATTGA | TGCGTTTGAT | 120
| TCAAGCCAAC | CCGGCATTAA | GTAAGCAGTT | GATGGAATAG | ACTTTTATCC | ACTTTATTGC | 180
| TGTTTACGGT | CCTGATGACA | GGACCGTTTT | CCAACGATT | AATCATAAAT | ATGAAAAATA | 240
| ATTGTTGCAT | CACCCGCCAA | TGCGTGGCTT | AATGCACATC | AACGGTTTGA | CGTACAGACC | 300
| ATTAAAGCAG | TGTAGTAAGG | CAAGTCCCTT | CAAGAGTTAT | CGTTGATACC | CCTCGTAGTG | 360
| CACATTCCTT | TAACGCTTCA | AAATCTGTAA | AGCACGCCAT | ATCGCCGAAA | GGCACACTTA | 420

( 2 ) INFORMATION FOR SEQ ID NO:14:

( i ) SEQUENCE CHARACTERISTICS:
        ( A ) LENGTH: 420 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

| | | | | | |
|---|---|---|---|---|---|
| GACAGGATTA | AAAATCGATG | ATTTCGCCCG | GGTTTTGGGC | GTATCAGTCG | CCATGGTAAA | 60
| GGAATGGGAA | TCCAGACGCG | TGAAGCCTTC | AAGTGCCGAA | CTAAAATTGA | TGCGTTTGAT | 120
| TCAAGCCAAC | CCGGCATTAA | GTAAGCAGTT | GATGGAATAG | ACTTTTATCC | ACTTTATTGC | 180
| TGTTTACGGT | CCTGATGACA | GGACCGTTTT | CCAACGATT | AATCATAAAT | ATGAAAAATA | 240
| ATTGTTGCAT | CACCCGCCAA | TGCGTGGCTT | AATGCACATC | AACGGTTTGA | CGTACAGACC | 300
| ATTAAAGCAG | TGTAGTAAGG | CAAGTCCCTT | CAAGAGTTAT | CGTTGATACC | CCTCGTAGTG | 360
| CACATTCCTT | TAACGCTTCA | AAATCTGTAA | AGCACGCCAT | ATCGCCGAAA | GGCACACTTA | 420

( 2 ) INFORMATION FOR SEQ ID NO:15:

( i ) SEQUENCE CHARACTERISTICS:
        ( A ) LENGTH: 420 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

-continued

```
GACAGGATTA AAAATCGATG ATTTCGCCCG GGTTTTGGGC GTATCAGTCG CCATGGTAAA      60

GGAATGGGAA TCCAGACGCG TGAAGCCTTC AAGTGCCGAA CTAAAATTGA TGCGTTTGAT     120

TCAAGCCAAC CCGGCATTAA GTAAGCAGTT GATGGAATAG ACTTTATCC ACTTTATTGC      180

TGTTTACGGT CCTGATGACA GGACCGTTTT CCAACCGATT AATCATAAAT ATGAAAAATA    240

ATTGTTGCAT CACCCGCCAA TGCGTGGCTT AATGCACATC AACGGTTTGA CGTACAGACC    300

ATTAAAGCAG TGTAGTAAGG CAAGTCCCTT CAAGAGTTAT CGTTGATACC CCTCGTAGTG   360

CACATTCCTT TAACGCTTCA AAATCTGTAA AGCACGCCAT ATCGCCGAAA GGCACACTTA   420
```

( 2 ) INFORMATION FOR SEQ ID NO:16:

( i ) SEQUENCE CHARACTERISTICS:
( A ) LENGTH: 420 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:16:

```
GACAGGATTA AAAATCGATG ATTTCGCCCG GGTTTTGGGC GTATCAGTCG CCATGGTAAA      60

GGAATGGGAA TCCAGACGCG TGAAGCCTTC AAGTGCCGAA CTAAAATTGA TGCGTTTGAT     120

TCAAGCCAAC CCGGCATTAA GTAAGCAGTT GATGGAATAG ACTTTATCC ACTTTATTGC      180

TGTTTACGGT CCTGATGACA GGACCGTTTT CCAACCGATT AATCATAAAT ATGAAAAATA    240

ATTGTTGCAT CACCCGCCAA TGCGTGGCTT AATGCACATC AACGGTTTGA CGTACAGACC    300

ATTAAAGCAG TGTAGTAAGG CAAGTCCCTT CAAGAGTTAT CGTTGATACC CCTCGTAGTG   360

CACATTCCTT TAACGCTTCA AAATCTGTAA AGCACGCCAT ATCGCCGAAA GGCACACTTA   420
```

( 2 ) INFORMATION FOR SEQ ID NO:17:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:17:

```
ACGAGCCGGA AGCATAAAGT GTAAATGTTT TTTATATGAA                            40
```

VECTORS AND TRANSFORMED HOST CELLS FOR RECOMBINANT PROTEIN PRODUCTION AT REDUCED TEMPERATURES

This application is a continuation in part of U.S. Ser. No. 08/278,281, filed on Jul. 21, 1994, now U.S. Pat. No. 5,654,169.

TECHNICAL FIELD OF THE INVENTION

The invention relates to an expression vector, the nucleic acid sequence of which comprises a promoter that is capable of controlling, when the vector is in a bacterial host and the temperature is lowered to below about 20° C., the production of recombinant peptide or protein encoded by a gene contained within the vector. The invention also relates to transformed host cells containing the vectors, and to a method of producing a recombinant protein.

BACKGROUND OF THE INVENTION

Genetic engineering provides methods for the cloning of foreign genes, their cDNA sequences or portions thereof, and their introduction into bacterial host cells such as *Escherichia coli*. The level of production of a foreign protein in the host cell depends on appropriately arranged transcription and translation control sequences that permit the regulated expression of the desired proteins or peptides coded by the foreign genes, gene fragments, various gene fusions or mutants thereof.

Transcription (i.e., the process leading to the production of mRNA) is a key step in the expression of a gene. Transcription initiation occurs at specific promoters which regulate gene expression. Promoters are regulated negatively by repressors and positively by activator proteins. The initiation of transcription can be separated into several steps (Buc et al., *Biochemistry* (1985) 24:2712). In order to act effectively, promoters are made of three elements. A core sequence is recognized by RNA polymerase. This region is flanked by the USR, or the upstream region, and the DSR, or the downstream region. The USR was shown to bind specific activator proteins (Adhya et al., *Gene* (1993) 132:1). Two modes of gene activation are generally considered. DNA-bound activator makes direct contact with RNA polymerase and thereby facilitates the binding and isomerization of RNA polymerase. Alternately, the bound activator changes the structure of the promoter, thereby favoring transcription initiation.

In order to maintain the desired foreign gene and to express it in a bacterial host cell at a high level for protein purification, it is essential to place the gene under the control of a regulated promoter that permits turning off of gene expression during the first stage of fermentation in which the cell mass is increased, and turning it on at the second fermentation stage in which maximal gene expression and protein production is needed.

Production of proteins utilizing a number of promoters and ribosome binding sites has been previously described. For example, the use of the pL promoter for regulated gene expression has been the subject of several references (e.g., Bernard et al., *Gene* (1970) 5:59; Derom et al., *Gene* (1982) 17:45; Gheysen et al., *Gene* (1982) 17:55; Hedgpeth et al., *Mol. Gen. Genet.* (1978) 163:197; Remaut et al., *Gene* (1981) 15:81; and Deryneck et al., *Nature* (1980) 287). A number of ribosome binding sites have been employed in order to obtain a high level of protein synthesis, such as the phage λ cII translation initiation region used for the production of cII (Oppenheim et al., *J. Mol. Biol.* (1982) 158:327; Shimatake et al., *Nature* (1981) 292:128). Similarly, production of human growth hormone (hGH) and bovine growth hormone (bGH) are described, inter alia, in U.S. Pat. No. 4,997,916.

One of the major problems in producing eukaryotic proteins in the bacterium *E. coli* is that the desired protein is often obtained in inactive aggregates termed inclusion bodies. The inclusion bodies can facilitate protein purification provided that it is possible to refold the desired peptide to the active protein form in vitro by some process (see, for example, U.S. Pat. No. 4,997,916). However, there are proteins for which in vitro refolding is highly inefficient.

Several factors appear to contribute to the formation of inclusion bodies. The most important of these are the rapid synthesis of a single protein following induction of gene expression in the fermentation process, and the temperature at which fermentation takes place. At high temperatures, refolding of the individual molecule is slowed down. The presence of a high concentration of incompletely folded proteins leads to protein aggregation due to the intermolecular interactions of hydrophobic domains. In production of the native protein, these hydrophobic domains play an important role in the folding of the protein into a fully active form.

At present, there is no known way to direct the production of proteins in their native form during the fermentation process. For some proteins (such as hGH and bGH) it is possible to disaggregate and refold the desired protein, while for others there is no known refolding process. However, it is known that chaperonin protein complexes can act to facilitate disaggregation in vivo. This process can also be carried out on a small scale in biochemical laboratories.

It has been shown that proteins expressed in *E. coli* at low temperatures have an increased solubility (Schein et al., *Bio/Technology* (1988) 6:291; Schein, *Bio/Technology* (1989) 7:1141). For example, when interferon (IFN-α2) was expressed in a bacterial culture at 37° C., 95% of the protein was found in inclusion bodies. In contrast, only 27% of the protein was insoluble when the same culture was grown at 30° C. Similar results were obtained for IfN-γ, and Shirano et al. (*FEBS* (1990) 1:128) demonstrated the low-level expression of soluble lipoxygenease in *E. coli* at about 15° C.

Accordingly, there remains a need for vectors which allow for the isolation of biologically active eukaryotic protein from bacterial cells. It is an object of the present invention to provide such vectors, as well as methods for the production and isolation of eukaryotic proteins from bacterial cells in a biologically active form. It is another object of the present invention to provide host-vector systems for the production of a desired protein in native form.

These and other objects and advantages of the present invention, as well as additional inventive features, will be apparent from the description of the invention provided herein.

BRIEF SUMMARY OF THE INVENTION

The present invention provides an expression vector, the nucleic acid sequence of which comprises a promoter that is capable of controlling, when the vector is in a bacterial host and the temperature is lowered to below about 20° C., the production of recombinant peptide or protein encoded by a gene contained within the vector.

The invention also relates to transformed host cells containing the vectors, particularly transformed *E. coli* host cells.

In addition, the invention relates to a method of producing in native active form a desired protein encoded by a gene contained within the vector.

BRIEF DESCRIPTION OF THE FIGURES

FIG. 7 depicts the DNA sequence of the EL cspA promoter, which is comprised approximately of the nucleotides between the arrows labeled "EL". The sequence of the EL cspA promoter contained in pIK-EL is set forth in SEQ ID NO:3 and 13.

FIG. 9 depicts the DNA sequence of the L cspA promoter, which is comprised approximately of the nucleotides between the arrows labeled "L". The sequence of the L cspA promoter contained in pIK-L is set forth in SEQ ID NO:4 and 14.

FIG. 13 depicts the DNA sequence of the S cspA promoter, which is comprised of the nucleotides between the arrows labeled "S". The sequence of the S cspA promoter contained in pIK-S is set forth in SEQ ID NO:6 and 16.

FIGS. 14A–14B depict (A) the presence of the cspA promoter in the plasmid pIK86 and its insertion into phage λB299 by means of a double crossover recombination event and (B) the resulting vector lambdaPcspA (λPcspA).

FIG. 18 depicts a partial restriction map of plasmid pHG309 (a derivative of plasmid pHG87) and pL-plac (which responds to the lac repressor and is enhanced by pL promoter elements).

FIG. 19 depicts the expression of lacZ, in terms of enzyme activities and messenger RNA level, under the control of various cspA promoters, at 37° and 15° C.

DETAILED DESCRIPTION OF THE INVENTION

Figure 1B:
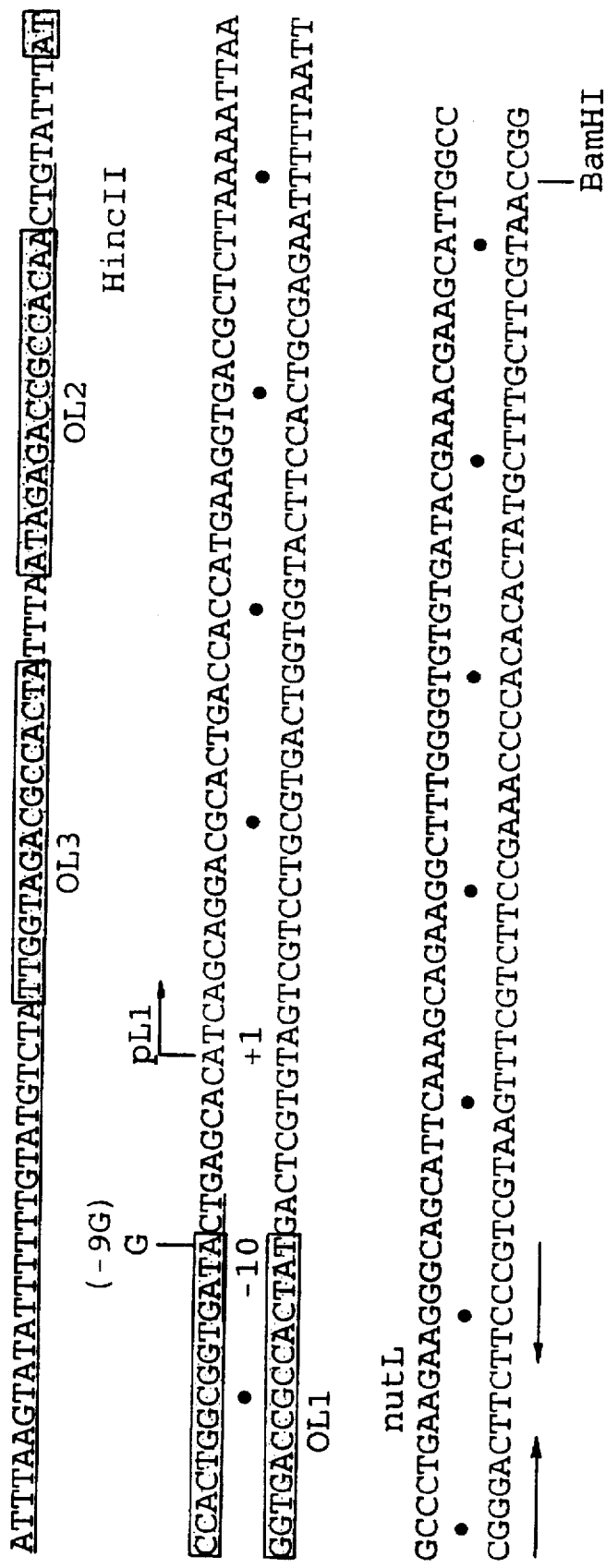
FIG. 1 depicts the DNA sequence of the pL promoter region including the nucleotides flanking the Eco RI and Bam HI sites (SEQ ID NO:12). This sequence is also set forth in SEQ ID NO:1.

The invention relates to expression vectors which lead to the high level expression of subcloned genes in bacterial host cells at low temperatures (i.e., at temperatures less than about 20° C.), and which allow the production of proteins in their native and active form.

The invention is based on the premise that the rate of protein folding will be only slightly affected by lowering the temperature to about 15°–20° C., while the rate of transcription and protein synthesis, being biochemical reactions, will be greatly slowed down (e.g. 5- to 10-fold). Exploitation of these conditions, as in the context of the present invention, allows individual proteins sufficient time to refold in an independent way, yielding active proteins and preventing the formation of aggregates, without reducing the final yield of the desired protein.

Accordingly, the invention provides vectors which allow for the production of native and active eukaryotic protein in a bacterial host cell.

Fermentation in bacterial host cells containing such vectors is based on a two-stage process. At the first stage there is rapid bacterial growth at high temperatures of about 37°–43° C. during which only a very low level of expression of a subcloned gene contained within the vector takes place. At the second stage there is an increase of gene expression of the subcloned gene upon transfer to the low temperature. Following fermentation, pure, soluble and highly active proteins can be isolated. The increased production of protein that occurs upon transfer of the host cells to low temperature requires utilizing the specifically designed expression systems which are the subject of the present invention. These vectors allow for increased gene expression and production of protein or peptides at a temperature below about 20° C.

By utilizing a high temperature for bacterial growth, the cell carrying the desired gene will grow rapidly without expressing the desired peptide. Following a change to lower temperature in the fermentation system, the expression of the gene encoding the foreign protein will be initiated. Finely tuning the rate of synthesis of the desired protein at low temperature yields high levels of soluble and biologically active proteins. This expression system is of general use and can be used for proteins such as viral proteins, especially those useful for preparing vaccines against viruses, in particular against hepatitis viruses such as hepatitus A, insulin, cytokines such as interleukins such as IL 1–13, in particular IL-2α, interferons, clotting factor genes such as Factors I-XIII, in particular VIII, hormones such as follicle stimulating hormones, any glucocerebrosidase such as β-glucocerebrosidase and other growth factors and, in principle, any desired protein or peptide.

The vectors of the present invention comprise a nucleic acid sequence which comprises a gene encoding a desired protein or peptide, as well as a promoter which is highly active at low temperature. These vectors, upon introduction to a bacterial host cell, enable the high level production of the desired protein or peptide at low temperatures. The protein or peptide is obtained in a native active form, and therefore no additional manipulation of the protein, such as protein refolding, is required.

Accordingly, the present invention provides an expression vector comprising a nucleic acid sequence which comprises a gene and a promoter that is capable of controlling, when the vector is in a bacterial host and the temperature is lowered to below about 20° C., the production of a recombinant peptide or protein encoded by the gene contained within the vector.

In the context of the present invention, a promoter is a DNA sequence that directs the binding of RNA polymerase and thereby promotes nascent mRNA synthesis. The DNA sequences of eukaryotic promoters differ from those of prokaryotic promoters which means that eukaryotic signals may not be recognized in prokaryotic systems, and vice versa. Accordingly, the promoters of the present invention allow transcription of a gene contained within the vector and, moreover, allow increased transcription at temperatures below about 20° C.

Generally the gene inserted into the vector will be foreign (i.e., a gene that is not normally expressed in the particular host in which the vector will be introduced), and, preferably, the gene will be of eukaryotic origin. The gene may be wholly or partially synthetic. The protein or peptide encoded by the gene may comprise a full length protein, a polypeptide, or a chimeric protein.

Also, the vectors of the present invention must be capable of replication in a bacterial host (i.e., either autonomously or as part of the host genome), and must be capable of directing the production of the peptide or protein in the bacterial host. Thus, the vectors preferably comprise appropriate control elements (e.g., promoters and ribosome binding sites) for commanding the production of the peptide or protein in the host.

In some cases, the gene contained within the vector and encoding the protein or peptide will contain the appropriate regulatory elements such that these elements need not be present on the vector. In other cases (such as when a eukaryotic protein is being produced in a prokaryotic host), it is preferred that the vectors of the present invention comprise these additional elements. It is preferred that all of the proper transcription and translation signal be correctly arranged on the vector, such that the foreign gene will be properly expressed within the host, and protein will be translated, when the temperature is decreased to below at 20° C.

Accordingly, preferably the expression vectors of the present invention further comprise an initiation codon (such as an ATG codon) positioned so as to allow translation of the peptide or protein to initiate from the initiation codon. Even more preferable is that the initiation codon be positioned between said promoter and said gene.

Also, preferably the expression vectors of the present invention further comprise a ribosome binding site positioned so as to control translation of said peptide or protein, preferably positioned between the promoter and the translation initiation codon.

The presence of these additional control elements on the vectors may be necessitated by the fact that translation in prokaryotes, just like transcription, also does not proceed well in response to eukaryotic signals. For instance, initiation of translation in prokaryotes requires the presence of an initiation codon, such as the ATG codon. If the foreign DNA does not comprise such a codon, one or more such codons can be provided in the vectors of the present invention. Preferably the initiation codon will be placed upstream from the sequences through which translation is to initiate, and downstream of the promoters of the present invention which impart increased transcription at low temperatures upon subcloned fragments placed under their control.

Similarly, the vectors of the present invention may also comprise a ribosome binding site (i.e., a "Shine-Dalgarno sequence"; Shine et al., *Nature* (1975) 254:34). It is known that efficient translation in prokaryotes is dependent on such a sequence, which exhibits complementarity to the 3' end of the 16S ribosomal RNA (rRNA), and likely promotes binding of mRNA to ribosomes by duplexing with the rRNA, thus allowing the correct positioning of the ribosome on the mRNA. Accordingly, it is preferable that the ribosome binding site be contained within the vectors of the present invention upstream of the translation initiation codon and downstream of the promoters which impart increased transcription at low temperatures upon subcloned fragments.

Preferably, the vectors of the present invention further comprise additional operably-bound DNA sequences which contain other control elements. For instance repressor sites involved in the turning off of gene expression and enhancers involved in the augmentation of gene expression are contemplated in the context of the present invention.

The vectors of the present invention comprise a nucleic acid sequence preferably comprising DNA, which may be single or double-stranded. The vectors may exist as plasmids, cosmids (i.e., plasmids comprised of a cos site) or bacteriophages. In preferred embodiments of the present invention, the vector comprises a plasmid, or a bacteriophage, or may comprise a plasmid:bacteriophage cointegrate which may further be inserted into the bacterial chromosome.

Preferred vectors of the present invention wherein the vector comprises a bacteriophage are: λPcspA (λA01131 deposited as ATCC No. 75718) and λA01107 (deposited as ATCC No. 75717). Other preferred vectors include but are not limited to pHG87 and pHG91.

While prokaryotic species such as the bacterium *E. coli* stop growing at about 10° C., the vectors of the present invention allow production at a temperature of less than about 20° C. (i.e., at about 15°–16° C.) of a high level of a peptide or protein encoded by a gene contained within the vector, for example, of the reporter gene lacZ.

The low temperature provides a way to regulate the level of gene expression, allowing the skilled artisan to find a temperature at which the expression rate will be reduced, and providing the maximal time needed for proper protein folding, thus preventing protein aggregation. In other words, as the rate of cell growth is slowed down at lower temperature, the relative time allowed for refolding of individual protein molecules will be increased.

The expression systems described herein are based on two different sets of promoters and regulatory elements. In one embodiment, the expression vectors according to the invention comprise the cold-sensitive pL promoter of phage λ. Descriptions in the literature of the use of the pL promoter of phage λ and its thermosensitive cI repressor mutant have been extensive. Typically, cells are first grown at 30° C. until a high cell mass is reached. At that stage, the cells are transferred to 42° C. and repression of the pL promoter is lifted, leading to the enhanced expression of a subcloned gene placed under the control of the pL promoter (see, e.g., Giladi et al., *J. Mol. Biol.* (1992) 227:985–990; Giladi et al., *J. Mol. Biol.* (1992) 224:937–948; Ptashne, *Genetic Switch: Phage Lambda and Higher Organisms* (Cell Press & Blackwell Scientific Publications, Cambridge, Mass. (1992)).

However, the present invention comprises a pL mutant promoter that is most active at a low temperature (i.e., a temperature less than about 20° C.). In addition it was discovered in the context of the present invention that the wild-type and improved mutants of the pL promoter (e.g., pL-9G-50) are also highly active at temperatures less than about 20° C.

A number of pL derivatives were constructed using conventional recombinant DNA techniques and tested for promoter response to low temperature as described in Example 2 below. A 3 base pair mutant at the region from −4 to +4 of the transcription start site (which altered the sequence from GCACATCA to GGACAAGA) diminished the cold-response. Other nucleotide substitutions at other sites within this region, in particular the sites appearing in bold text, should provide similar results. A similar reduction in the cold-response was obtained when sequence at the −10 region of the pL promoter was changed from GATACT to TATAAT. Other nucleotide substitutions at other sites within this region, in particular the sites appearing in bold text, should provide similar results. A −9G mutation (in which the sequence GATACT was changed to GATGCT) resulted in a significant response upon transfer to low temperature. Other nucleotide substitutions at other sites within this region, in particular the site appearing in bold text, should provide similar results.

pHG309, a pL promoter derivative in which an internal deletion, spanning nucleotides −40 to −70, was introduced, retains the response to low temperature but does not require IHF for full activity. To obtain the −40 to −78 deletion, two successive PCR reactions were used. In the first reaction, a pL fragment extending from −130 to −79 and carrying at the 3' end an additional 12 base pairs from −39 to −28, was engineered usng primers #1815 (5'-TCAGAATTCTCACCTACC-3' SEQ ID NO:9) and #2319 (5'-TATGTCAACACCTTTTTTATATG-3') (SEQ ID NO:10). In the second reaction, primers #2011 (5'-AAGGATCCAATGCTTCGTTT-3' SEQ ID NO:11) and the product of the first PCR reaction were used. This promoter was found, when present on a multicopy plasmid, to be about 7 to 15 fold more active than the −9G-50 mutant, depending on growth conditions (as assayed by β-galactosidase activity). It is expected that other mutants which contain lesser deletions in this same area (so long as the open reading frame is maintained) will similarly retain low temperature responsiveness and may also may not require IHF for full activity.

The pL-Plac chimeric promoter was generated in a similar way, using primer #1815 and a chimeric primer #4402 (5'-ACGAGCCGGAAGCATAAAGTGTAAATGTTTTTT-ATATGAA-3' SEQ ID NO:17) on a pL template in the first PCR reaction. In the second reaction, the product of the first reaction was used as the ustream primer. The universal M13 primer was employed and the Plac promoter served as template. In this fusion product, expression is regulated by the lacI repressor and can be induced by IPTG. The region from −130 to −79 of pL was fused to Plac (from −36 to +84). The response of this promoter to low temperature was not tested.

In another embodiment, the expression vectors of the invention comprise the cspA promoter. This promoter is highly responsive to low temperatures, and, in its native position in the bacterial chromosome, directs the synthesis of over 13% of the bacterial proteins synthesized (Tanabe et al., *J. Bacteriol.* (1992) 174:3867; Goldstein, *Proc. Nat. Acad. Sci.* (1990) 87:283). The cspA gene is the major cold shock gene that has been described in bacteria (Goldstein et al., *Proc. Natl. Acad. Sci.* (1990) 87:283; Jones et al., *J. Bacteriol.* (1992) 174:3903; Tanabe et al., *J. Bacteriol.* (1992) 174:3867).

The promoter region of the cspA gene has been dissected, allowing the identification of a number of regions involved in the enhancement of transcription. The strength of this promoter allows certain clones to be maintained only at high temperatures. The influence of the cspA promoter on lacZ expression in the context of the present invention was confirmed as illustrated in the Examples.

A spontaneous mutation in the −35 region (a T:A to C:G mutation at −36) greatly increases the partition of expression between high and low temperature (and see FIG. 19). It is expected that any nucleotide substitution at this position would provide similar results. It is further expected that other mutations ±5 of the −35 site will provide similar results.

Accordingly, preferred vectors of the present invention comprise a pL promoter or a PcspA promoter. The pL promoter and PcspA promoter may further comprise a mutation or mutations. In the context of the present invention, a mutation results in an alteration of the DNA sequence, and may consist of an addition, deletion or substitution in the base sequence. Some mutations of the PcspA promoter according to the present invention are contained within, for example, pIK-L and pIK-M. Similarly, a pL mutation according to the present invention is contained within pL-9G-50.

Other preferred vectors of the present invention comprise vectors in which the promoter comprises the sequence of: SEQ ID NO:1; SEQ ID NO:2; SEQ ID NO:3; SEQ ID NO:4; SEQ ID NO:5; or SEQ ID NO:6.

Other preferred vectors include: λA01107 contained within the cell line deposited with the ATCC and assigned No. 75717; λPcspA contained within the cell line deposited with the ATCC and assigned No. 75718; pIK-M contained within the cell line deposited with the ATCC and assigned No. 75719; pIK-EL contained within the cell line deposited with the ATCC and assigned No. 76720; and the plasmids pIK-L and pIK-P.

The present invention further relates to a host-vector system for the production of a desired protein in native active form which comprises an expression vector according to the present invention in a suitable bacterial, and preferably *E. coli*, host cell.

Also, the expression of the pL promoter is positively regulated by HIF, which is a natural component of *E. coli* host cells. Accordingly, HIF⁺ *E. coli* strains, which contain the known host integration factor, HIF, are preferred for use with the vectors of the present invention comprising the pL promoter.

Generally, even more preferred *E. coli* strains are those which contain mutations that will increase the level of protein production and/or stability, or will correct the folding of the desired gene products. Such strains are, for example, mutants defective in the lon or hfl genes, which may improve stability by reducing proteolysis. Additionally, preferred strains may comprise mutations in recA or other recombination/repair genes, such mutations which are known to be involved in recombination, including deletions, of eukaryotic DNA contained within bacterial hosts.

Accordingly, the present invention provides a bacterium containing the vector in which the promoter comprises the sequence of: SEQ ID NO:1; SEQ ID NO:2; SEQ ID NO:3; SEQ ID NO:4; SEQ ID NO:5; or SEQ ID NO:6.

Similarly, the present invention comprises a nucleic acid comprising a vector in which the promoter comprises the sequence of: SEQ ID NO:1; SEQ ID NO:2; SEQ ID NO:3; SEQ ID NO:4; SEQ ID NO:5; or SEQ ID NO:6.

Other preferred host-vector systems for the production of β-gal in native active form comprise the λPcspA or λA01107 expression vectors in a suitable *E. coli* host cell, particularly strain A7506.

In a preferred host-vector system, the gene encoding the desired protein or peptide is integrated into a suitable *E. coli* host cell chromosome through use of the phage λ expression vectors. Integration into the chromosome results in a single copy of the gene fusion which is extremely stable, and which allows for performing the fermentation procedure without the use of antibiotics.

Genes can be stably introduced into the bacterial chromosome using the method of the present invention. Under these conditions, the pL promoter can be maintained in the cell in the absence of the cI repressor. A low level of expression is found when the cells are grown at elevated temperatures, and a high level of expression is found when the cells are transferred to a low temperature.

In order to further improve the system so as to allow the use of plasmids and further increase protein production, a mutant repressor that is active at high temperature but not at low temperature can be incorporated within the *E. coli* chromosome or subcloned into a plasmid vector. When supplied with this mutant repressor, cell cultures could be grown at 37° C. before being transferred to lower temperature to allow for the expression of the cloned gene. It is possible to use the system as plasmids. It is possible that to acquire greater protein stability, the host has to be grown at 42° C. before lowering the temperature. It is probable that specific growth conditions will have to be developed, depending on the gene to be expressed. Thus, homologous recombination is not essential.

In contrast to the pL promoter, positive or negative regulators of the cspA promoter have not been identified. Using the appropriate promoter constructs according to the present invention, it is possible to directly manipulate promoter activity. Cells carrying proper fusions will be grown at 37° C. or higher temperatures, and fusions will be induced by a change in the culture temperature (i.e., lowering the temperature below about 20° C.).

The present invention further provides a method of producing a desired protein encoded by a subcloned gene contained within an expression vector which comprises introducing the expression vector into a suitable host cell, preferably a bacterial host cell, maintaining the cell in culture, and isolating the protein produced.

Cell expansion is facilitated by growing cells between 15° to 45° C. Preferably the cell is maintained in culture at a temperature of about 37° C. for a suitable length of time to allow an increase in cell growth, and is then maintained in culture at a temperature below about 20° C. (between 10° and 20° C.) for a suitable length of time to allow production of protein. Cells are grown at elevated temperature followed by transfer to low temperature, while sampling at four hour intervals (up to 72 hours) in order to determine the highest activity. Samples are also evaluated by protein gel electrophoresis.

Isolation of protein can be by any technique known in the art for the purification of proteins, such as chromatography, centrifugation, differential solubility, isoelectric focusing, etc. However, preferably the foreign protein will be obtained from the bacterial host cell by suitable means whereby the protein is recovered in native active form. Cells are harvested and lysed using standard procedures. It is possible that specific buffer conditions will be required to prevent in vitro aggregation of protein.

Standard culture media, rich or minimal, can be used in the context of the present invention. As mentioned above, with suitable vectors, addition of antibiotics to the culture media can be avoided, which may be of particular advantage for production of certain proteins.

The following examples further illustrate the present invention but, of course, should not be considered as in any way limiting its scope.

EXAMPLE 1

Materials and Methods Employed in Experiments

Bacterial strains, phages and plasmids

In the present experiments, standard molecular and genetic techniques such as generation of strains, phages and plasmids, gel electrophoresis, DNA manipulations including cloning and sequencing, primer extension assays, etc., were performed such as are known to those skilled in the art and are described in detail in standard laboratory manuals (e.g., Maniatis et al., *Molecular Cloning: A Laboratory Manual*, 2nd ed. (Cold Spring Harbor, N.Y., 1992); Ausubel et al., *Current Protocols in Molecular Biology*, (1987); Miller, *A Short Course in Bacterial Genetics*, (Cold Spring Harbor, N.Y., 1992)). Restriction enzymes and other enzymes used for molecular manipulations were purchased from commercial sources, and used according to recommendations. Strains were cultured, and phages were maintained, propagated and titered using standard reagents, media and techniques (Maniatis et al., *Molecular Cloning: A Laboratory Manual*, 2nd ed. (Cold Spring Harbor, N.Y., 1992); Miller, *Experiments in Molecular Genetics* (Cold Spring Harbor Laboratory Press, Cold Spring Harbor, N.Y., 1972)). Preferably, Luria-Bertani (LB) Medium containing Bacto tryptone (10 g/l), Bacto yeast extract (5 g/l) and NaCl (10 g/l) was employed for growth of cells.

*E. coli* strain A7506 is a derivative of CSH50 (ara Δ(lac-pro) strA thi; described in Miller, *Experiments in Molecular Genetics* (Cold Spring Harbor Laboratory Press, Cold Spring Harbor, N.Y., 1972)) which carries the λA01107 prophage. Strains A7507, a hip3::cat derivative of A7506, and A7533, a himA82:Tn10 derivative of A7507, were generated by P1vir transduction.

Strain A6826 is a CSH50 derivative. Strain CSH50 was found to grow slowly on minimal medium plates containing the supplements vitamin $B_1$ and proline. A fast growing colony of CSH50 was isolated, purified and designated A6826. Strain 7833 is a λcspA EL-lacZ derivative of A6826 and strain 7832 is a λcspA S-lacZ derivative of A6826.

Figure 2:
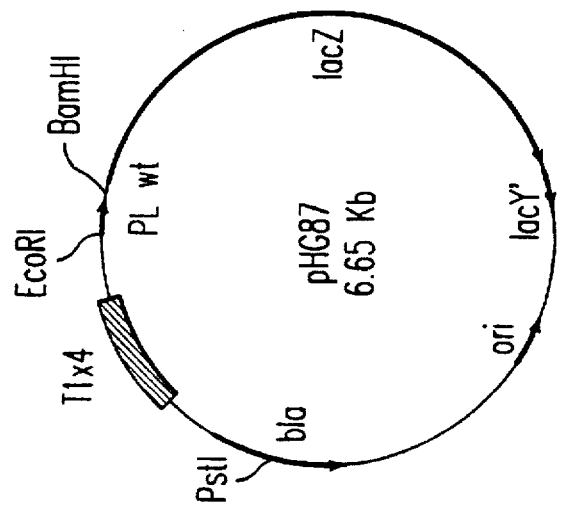
FIG. 2 depicts the restriction map of plasmid pHG87, which contains the wild-type pL promoter.

The DNA sequence of the pL promoter region including the nucleotides flanking the Eco RI and Bam HI sites is shown in FIG. 1, and is set forth in SEQ ID NO:1. Plasmid pHG87 contains the fragment comprising the wild-type pL promoter, as shown in FIG. 2.

Figure 3:
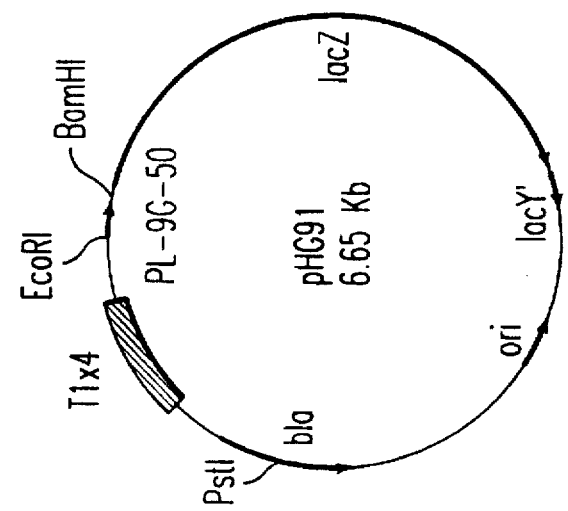
FIG. 3 depicts the restriction map of the plasmid pHG91, which contains the mutant pL promoter pL-9G-50. The sequence of this promoter is also set forth in SEQ ID NO:2.

The restriction map of plasmid pHG91 is shown in FIG. 3. Plasmid pHG91 contains the mutant pL promoter pL-9G-50. The sequence of this mutant promoter is characterized by an (A:T) to (G:C) mutation at basepair 220, and a GGCC sequence substituting AATT at basepairs 177–180, and is set forth in SEQ ID NO:2.

Plasmid pHG91 was obtained by fusing the pL-9G-50 promoter to the lacZ reporter gene present in plasmid pHG86 (Giladi et al., *J. Mol. Biol.* (1992) 224:937–948). A kanamycin resistance gene (Km$^R$) was then inserted in the Pst I restriction site located within the bla gene of pHG91 to generate plasmid pHG91K. When in full length form, the lacZ gene encodes β-galactosidase (β-gal) and the bla gene (sometimes designated amp) encodes a β-lactamase and confers host cell resistance to ampicillin.

Figures 4A, 4B:
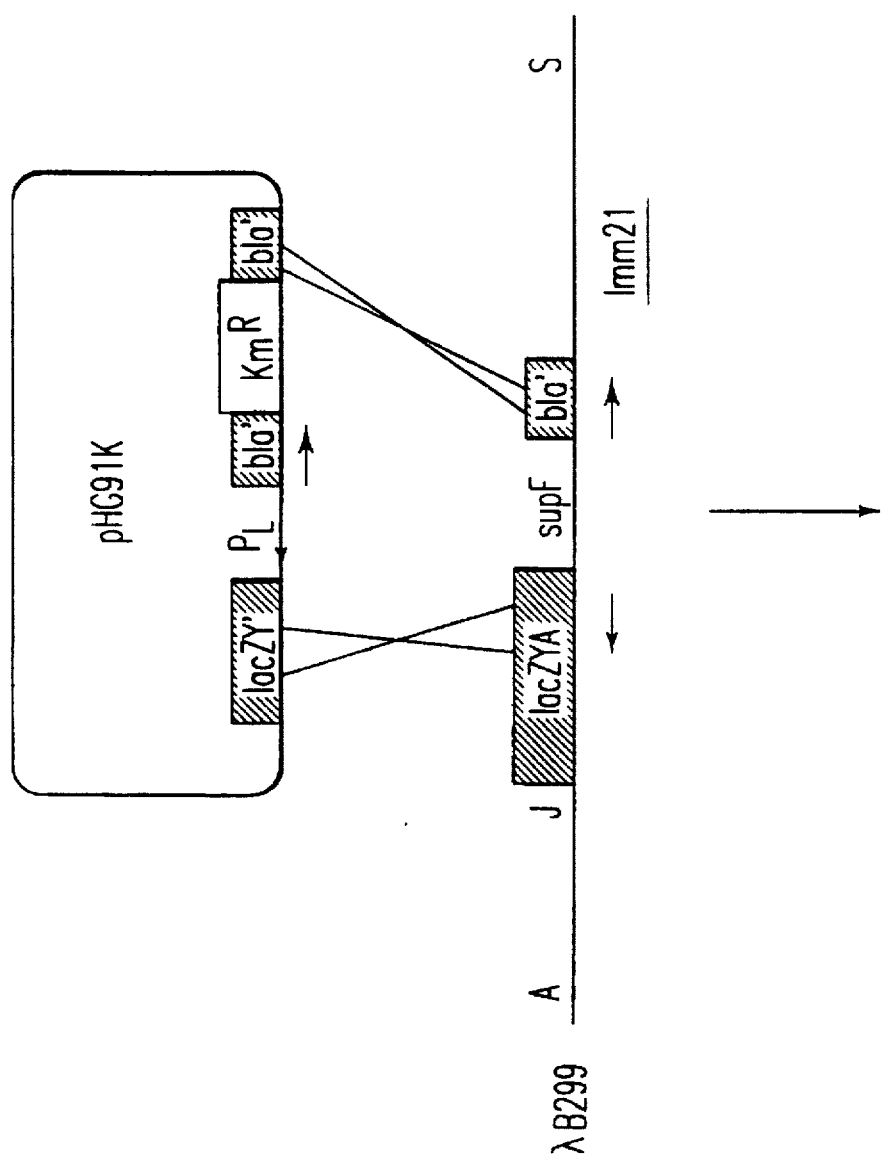
FIGS. 4A–4B depict (A) the presence of the mutant pL promoter pL-9G-50 in the plasmid pHG91K and its insertion into phage λB299 by means of a double crossover recombination event and (B) the resulting vector lambdaA01107 (λA01107).

Phage λA01107 is the product of recombination between phage λB299 and plasmid pHG91K, as set forth in FIG. 4. Phage λB299 (obtained from R. Weisenberg, Section on Microbial Genetics, Laboratory of Molecular Genetics, National Institutes of Health) carries the supF gene flanked by the truncated lacZ and bla genes. Recombination between phage λB299 and plasmid pHG91K results in the replacement of the supF gene by the pL-lacZ fusion from pHG91K in phage λA01107.

Plasmids phip$^+$, pR87G and pA90D are pEMBL18 derivatives, carrying the wild-type hip gene and its mutant alleles βR87G and βA90D (Menegeritsky et al., *J. Mol. Biol.* (1993) 231:646–657).

Figure 5:
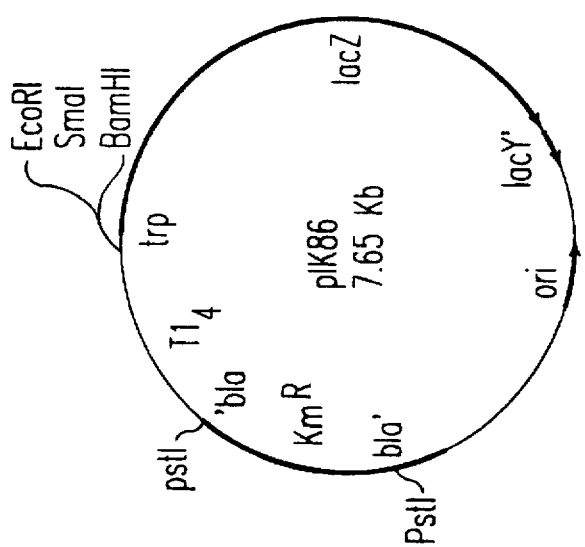
FIG. 5 depicts the restriction map of the kanamycin resistant (Km$^R$) plasmid pIK86 which was employed in construction of expression vectors according to the invention.

The cspA promoter fragment (309 bp in length from positions −214 to +95; Goldstein et al., *PNAS* (1990) 87:283–287) was cloned using the polymerase chain reaction (PCR; *PCR Protocols, A Guide to Methods and Applications*, Innis et al., eds., Academic Press, Inc. (1990)), and was inserted into the plasmid pHG86 upstream of the reporter lacZ gene. Plasmid pIK86 (shown in FIG. 5) was constructed from pHG86 by inserting Km$^R$ within the bla gene. A set of constructs containing different sized portions of the cspA promoter region was then prepared from pIK86. The different size fragments carrying the pcspA promoter region were each generated by PCR using a lambda phage carrying the cspA chromosomal region. Two primers were also employed: a primer homologous to the 5' region and carrying an Eco RI restriction site; and a primer homologous to the 3' region and carrying a Bam HI restriction site. The restriction maps of the cspA promoter constructs generated were determined.

Figure 10:
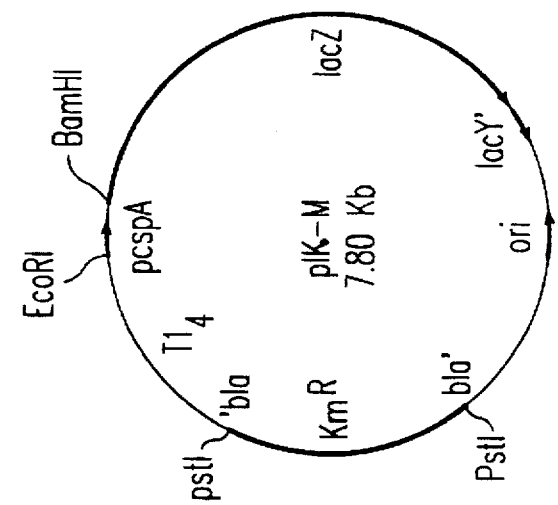
FIG. 10 depicts the restriction map of the plasmid pIK-M, which contains the M cspA promoter.
Figure 8:
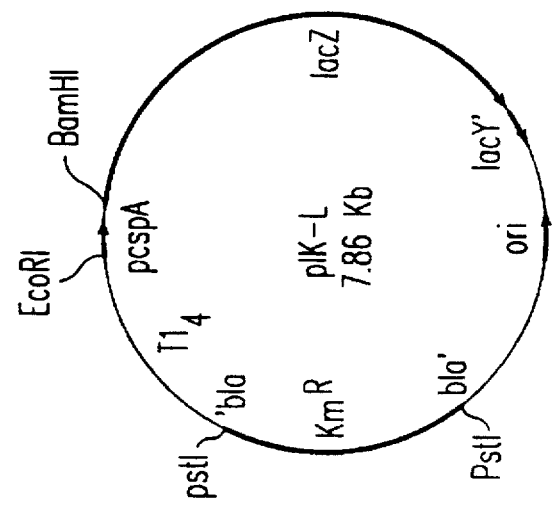
FIG. 8 depicts the restriction map of the plasmid pIK-L, which contains the L cspA promoter.
Figure 6:
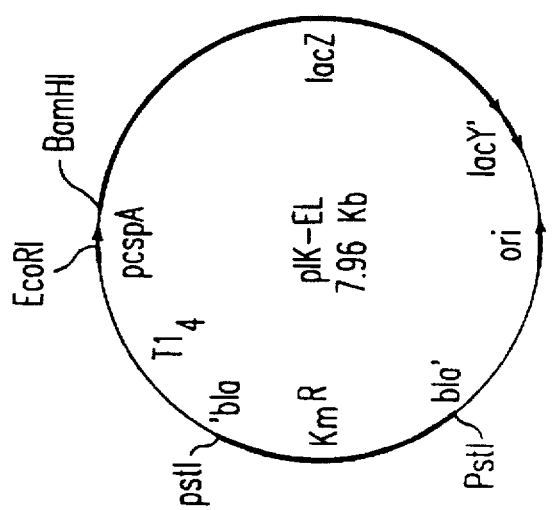
FIG. 6 depicts the restriction map of the plasmid pIK-EL, which contains the EL cspA promoter.
Figure 11B:
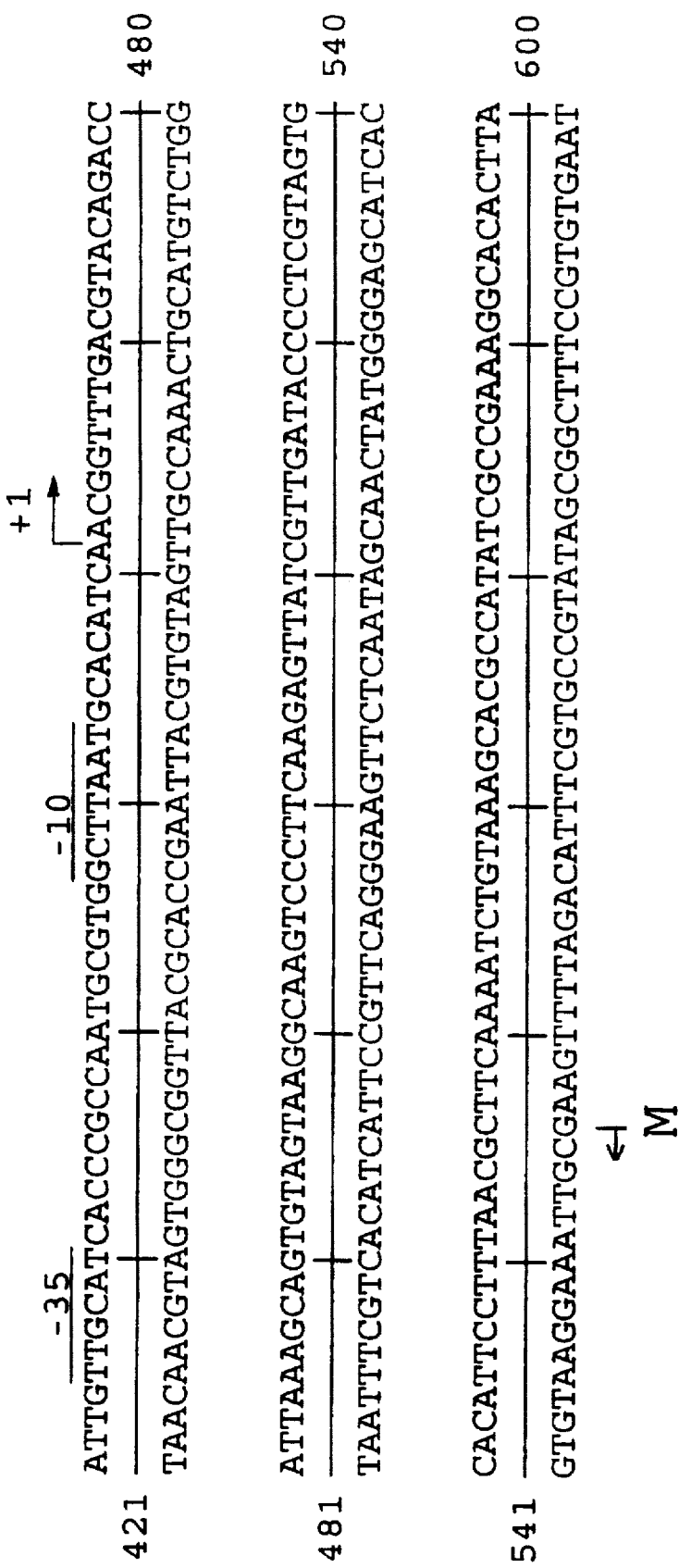
FIG. 11 depicts the DNA sequence of the M cspA promoter, which is comprised approximately of the nucleotides between the arrows labeled "M". The sequence of the M cspA promoter contained in pIK-M is set forth in SEQ ID NO:5 and 15.
Figures 12, 14:
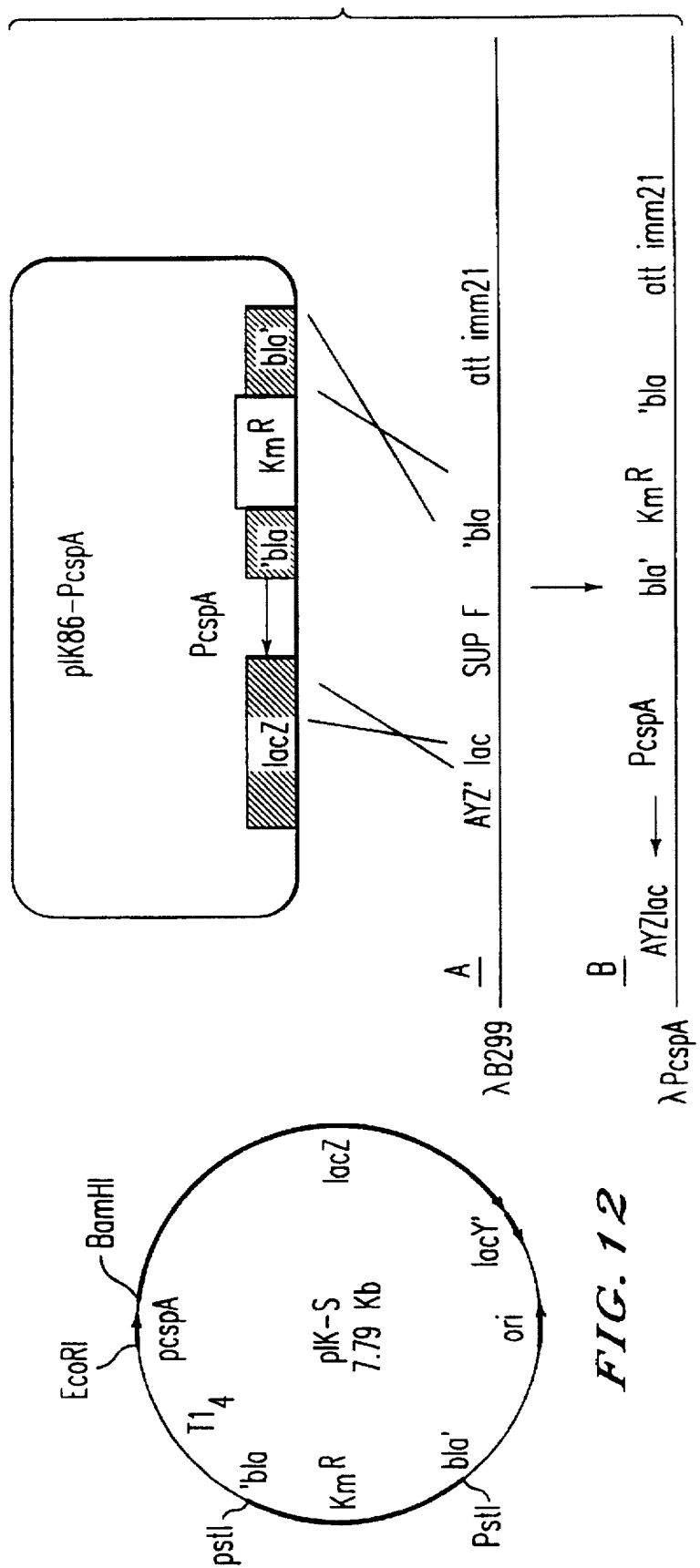
FIG. 12 depicts the restriction map of the plasmid pIK-S, which contains the S cspA promoter.

Of the cspA promoter region-containing plasmids, pIK-EL contains the largest upstream cspA promoter region, as indicated in FIG. 6. The sequence of the cspA fragment subcloned in the pIK-EL vector is given in FIG. 7 and SEQ ID NO:3. A smaller cspA promoter fragment was subcloned into pIK-L, as indicated in FIG. 8. The sequence of the cspA fragment subcloned in the pIK-L vector is given in FIG. 9 and SEQ ID NO:4. Similarly, pIK-M contains a still smaller cspA fragment, as indicated in FIG. 10. The sequence of the cspA fragment subcloned in the pIK-M vector is given in FIG. 11 and SEQ ID NO:5. The smallest cspA promoter fragment was subcloned into pIK-S, as indicated in FIG. 12. The sequence of the cspA fragment subcloned in the pIK-S vector is given in FIG. 13 and SEQ ID NO:6.

Since cspA is a strong promoter, in order to reduce the level of expression being driven by the scpA promoter at high temperatures, these constructs were subsequently transferred to phage λ by homologous recombination, as set forth in FIG. 14. The phage was then integrated into an *E. coli* chromosome. All crosses between plasmids and λB299 were carried out in strain A6826.

Preparation of DNA Fragments

DNA fragments used for the primer extension assay were obtained by PCR using Taq Polymerase (Promega Corp. Madison, Wis.). To obtain the 275-bp pL DNA fragment, primer 1921 5'-AAGAATTCGGGTTTTCTTT-3' (pL positions −228 to −217 as set forth in SEQ ID NO: 7), primer 1526 5'-AAGAGCGTCACCTTC-3' (pL positions +40 to +26 as set forth in SEQ ID NO: 8) and plasmid pHG244 DNA as a template were employed (Giladi et al., *J. Mol. Biol.*, (1992) 224: 937–948). All DNA fragments were end-labeled with (γ$^{32}$P)ATP (Amersham Corp., Arlington Heights, Ill.) and purified on a 5% polyacrylamide gel.

Enzymatic assays

Assays of β-gal specific activity were carried out according to Miller (Miller, *Experiments in Molecular Genetics* (Cold Spring Harbor Laboratory Press, Cold Spring Harbor, N.Y., 1972)).

EXAMPLE 2

Temperature Response of the pL promoter

To test the influence of temperature on gene expression driven by the attenuated pL-9G-50 promoter, this promoter was fused to the lacZ gene and inserted into the *E. coli* chromosome at the att site using phage λ, and generating strain A7506.

Figure 15:
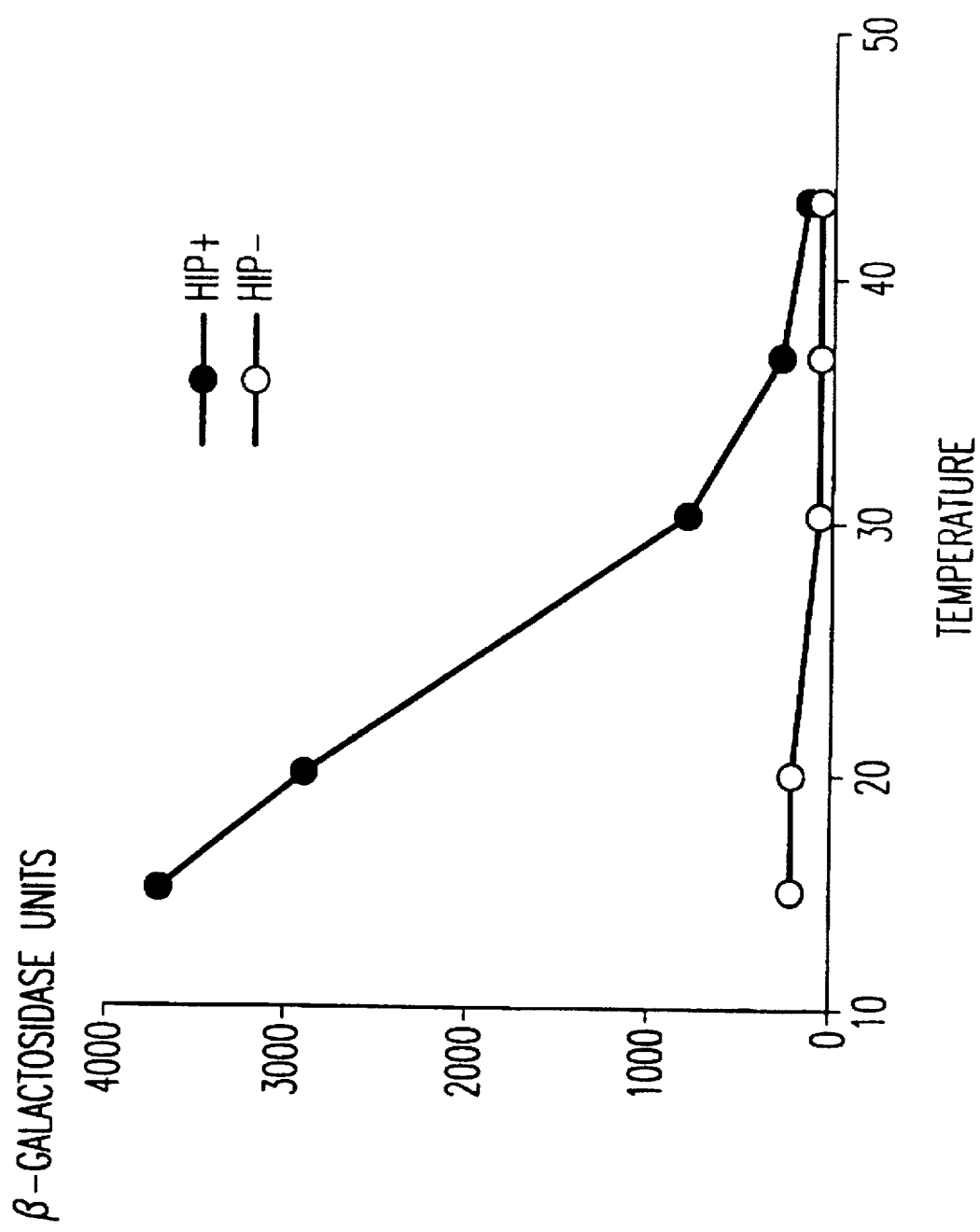
FIG. 15 depicts the temperature response of the pL-9G-50 promoter fused to a lacZ reporter gene and integrated in the bacterial chromosome in the presence (i.e., hip$^+$, ●) and absence (i.e., hip$^-$, ○) of the positive regulator of the pL promoter, host integration factor.

Cultures of strain A7506 were grown in LB medium at various temperatures to saturation, and were assayed for β-gal activity. As can be seen from FIG. 15, the levels of β-gal present in the cell were quite high at low temperatures (i.e., less than about 20° C.) and declined precipitously with increases in temperature. This temperature effect was not observed when cultures of strain A7507 were employed. Strain A7507 is a hip$^-$ derivative of strain A7506 which does not produce host integration factor, a positive regulator of the pL promoter. In strain A7507, levels of β-gal were low at all temperatures.

These results confirm that gene expression driven by the pL-9G-50 promoter is induced by low temperatures.

EXAMPLE 3

Temperature Shift Experiments

To study the response of the attenuated pL-9G-50 promoter to temperature changes, temperature shift experiments of the lacZ fusion of this promoter present in the chromosome of strain A7506 were performed.

For these experiments, cultures of strain A7506 (hip$^+$) and A7507 (hip$^-$) were grown exponentially at 37° C. or about 15°–16° C., and were then transferred to the alternate temperature (i.e., a culture grown at 37° C. was transferred to about 15°–16° C., and a culture grown at about 15°–16° C. was transferred to 37° C.). Levels of β-gal as well as cell density were determined at different times after the temperature shift.

Figure 16A:
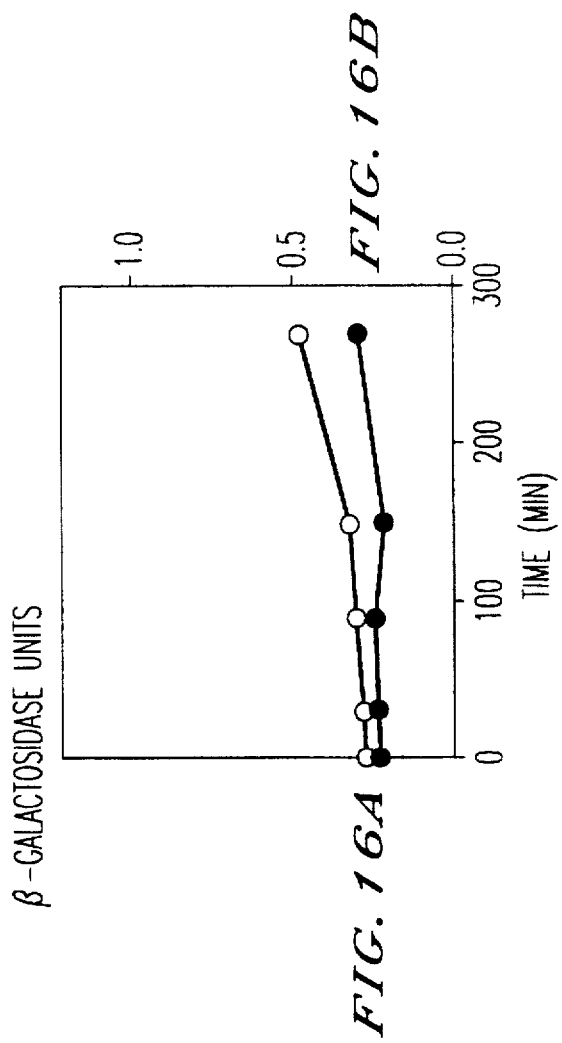
FIGS. 16a–16d depict the temperature response of the pL-9G-50 promoter fused to a lacZ reporter gene and integrated in the bacterial chromosome in the presence (i.e., hip$^+$, ●) and absence (i.e., hip$^-$, ○) of host integration factor. Cultures transferred from 37° C. to about 15°–16° C.: (a) β-gal levels, (b) cell density. Cultures transferred from about 15°–16° C. to 37° C.: (c) β-gal levels, (d) cell density.
Figure 16B:
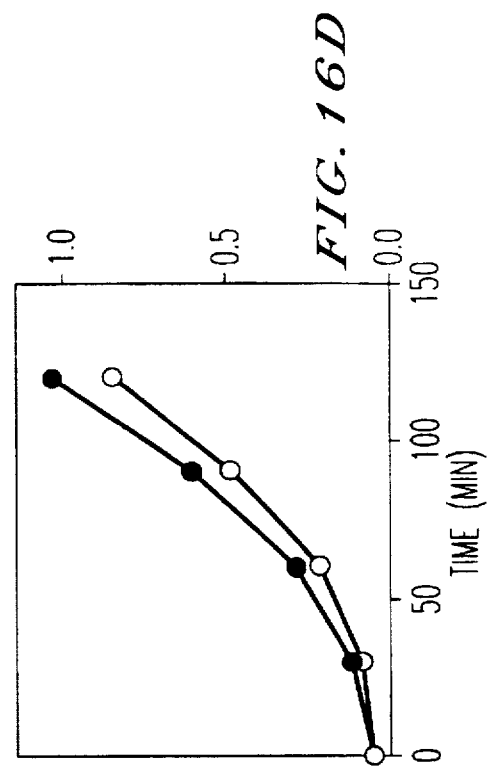

When exponentially growing A7506 cells were transferred from 37° C. to 15°–16° C., a dramatic increase in β-gal levels was observed as indicated in FIG. 16a. This increase occurred despite the long lag in cell growth due to the cold shock, as demonstrated in FIG. 16b, and was dependent on the presence of the wild-type hip gene, as it was not observed for the A7507 cells under the same conditions.

Figure 16C:
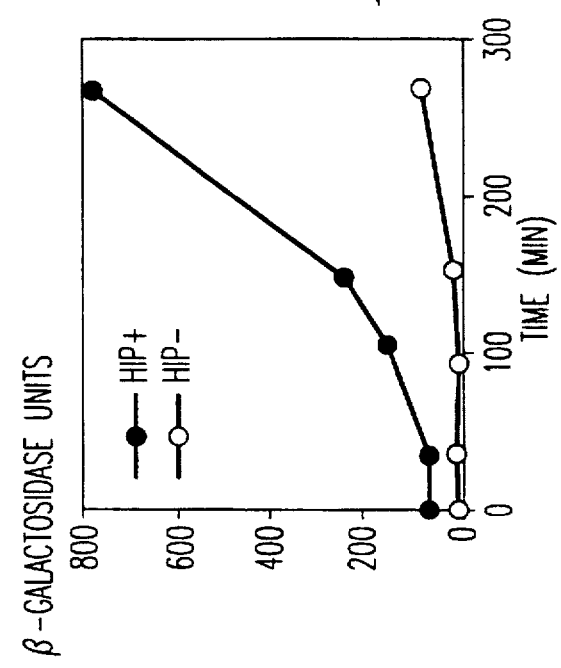
Figure 16D:
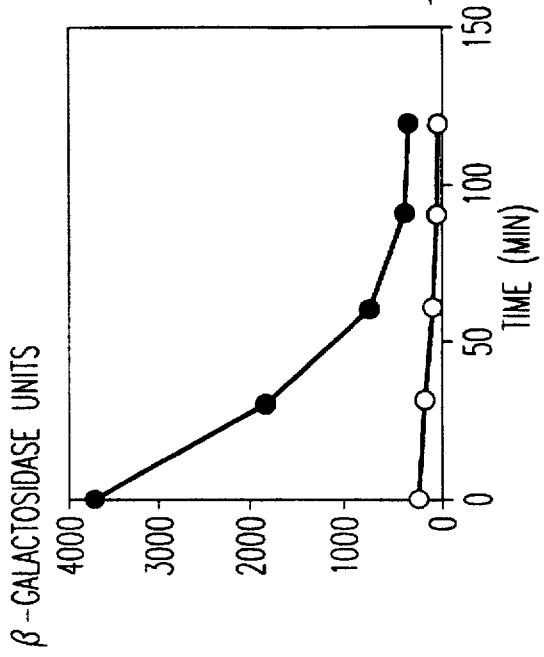

In contrast, when exponentially growing A7506 cells were transferred from 15°–16° C. to 37° C., a rapid cessation in β-gal specific activity was observed, as indicated in FIG. 16c. This decrease in β-gal specific activity correlates with the dilution of the existing enzyme by cell division (as indicated in FIG. 16d), possibly because transcription from pL was turned off rapidly after transfer to the higher temperature.

These results confirm that the attenuated pL-9G-50 promoter is able to drive a high level of gene expression upon transfer from 37° C. to about 15°–16° C.

EXAMPLE 4

Effect of Temperature on Promoter Activity

The pL-9G-50 and PcspA promoters were each fused to the lacZ gene in an operon fusion, transferred to phage λB299 by homologous recombination, and inserted at the att site of the bacterial chromosome as described above. Strain N99 was employed as a control to measure plac activity from its authentic operon (Ueshima et al., *Mol. Gen. Genet.* (1989) 215:185–189). These experiments were done to determine whether the temperature response of the pL promoter is unique to that promoter.

For these experiments, cell cultures were grown to saturation in LB medium at 37° C. or about 15°–16° C., and were then assayed for β-gal activity. Results are as summarized in Table 1.

TABLE 1

| Promoter | β-gal units | |
|---|---|---|
| | 15–16° C. | 37° C. |
| pL-9G-50 | 3860 | 260 |
| plac | 5950 | 7320 |
| PcspA | 1430 | 85 |

These results confirm that the PcspA promoters as well as the pL-9G-50 promoter are able to drive a high level of gene expression at low temperatures (i.e., less than about 20° C.). Expression driven by these promoters at about 15°–16° C. approaches that driven by the strong promoter plac. In contrast, expression of plac is reduced about 10–20% at 15°–16° C. as compared with at 37° C.

These results suggest that the higher enzyme levels observed for the pL promoter at low temperatures are due to increased pL transcription rather than to increased stability of the enzyme, or to more efficient protein translation. Contrary to the plac promoter, the cspA promoter was 20-fold more active at 15°–16° C. than at 37° C. It is noteworthy that the pL promoter showed the same temperature activation profile as PcspA. This temperature response is an intrinsic property of the pL promoter, and individual promoters appear to have an inherent response to temperature which is embedded within the promoter DNA sequence. The extent of response of the pL promoter to low temperatures, i.e., 14-fold higher at 15°–16° C. than at 37° C., is similar to that of the cspA promoter, yet these two promoters do not share DNA sequence similarities that indicate why they are more active at low temperature.

Thus, the pL-9G-50 and PcspA promoters minimally drive gene expression at temperatures at which bacterial cell growth and replication is optimized (i.e., at about 37° C.). This validates that the promoters can be employed to obtain maximal gene expression at temperatures at which bacterial cell growth and replication are minimized (i.e., less than about 20° C.).

EXAMPLE 5

Single Copy Chromosomal Fusion by Recombination between Phage λ and Plasmid

Similar experiments as in Example 4 done with the various pIK-cspA constructs confirm that these also are strong promoters, and that in fact, the EL and L constructs are difficult to maintain in host cells, possibly due to lethality as a consequence of a high level of gene expression. In order to reduce the level of expression driven by the cspA constructs at high temperatures, the constructs were transferred to phage λB299 by homologous recombination (as indicated in FIG. 14A–B). The resultant phages were then integrated into the bacterial chromosome, resulting in a single copy per cell.

As can be seen from Table 2, gene expression driven by the various cspA promoters as reflected in β-gal levels is temperature-regulated and is rather high in the resultant strains even though these strains contain only a single copy of the lacZ gene fusions.

TABLE 2

| Single Copy | β-gal Units | |
|---|---|---|
| | about 20° C. | 37° C. |
| λIK-EL | 20000 | 1000 |
| λIK-M | 24000 | 2000 |
| λIK-S | 9000 | 900 |
| λIK-P | 11170 | 2440 |

The single copy system is extremely stable and allows for performing the fermentation procedure without the use of antibiotics. Similar results to those as shown above for the pL promoter demonstrate that the pL wild-type promoter, which cannot be maintained in the absence of repressor, can direct the expression of lacZ in a single copy.

These results confirm that the various cspA promoters (as well as the pL-9G-50 promoter) can effectively drive gene expression at low temperatures resulting in a high level of translated protein when present as only a single copy integrated into the bacterial chromosome.

EXAMPLE 6

Influence of PcspA promoter on lacZ Expression at Low Temperatures

To test the PcspA promoter influence on lacZ expression, cells carrying the EL-lacZ fusion (i.e., strain A7833), the M-lacZ fusion (i.e., strain A7831) and the S-lacZ fusion (i.e., strain A7832) on phage λ as a single copy in the bacterial chromosome, were examined.

For these experiments, cultures were grown in LB at 37° C., and were transferred to about 15°–16° C. at time 0. Samples were taken at 1, 2, 4 and 6 hours intervals, and RNA was isolated and assayed by primer extension using labeled primers and reverse transcriptase. Radioactivity of the band corresponding to the transcription start site was determined.

Figure 17:
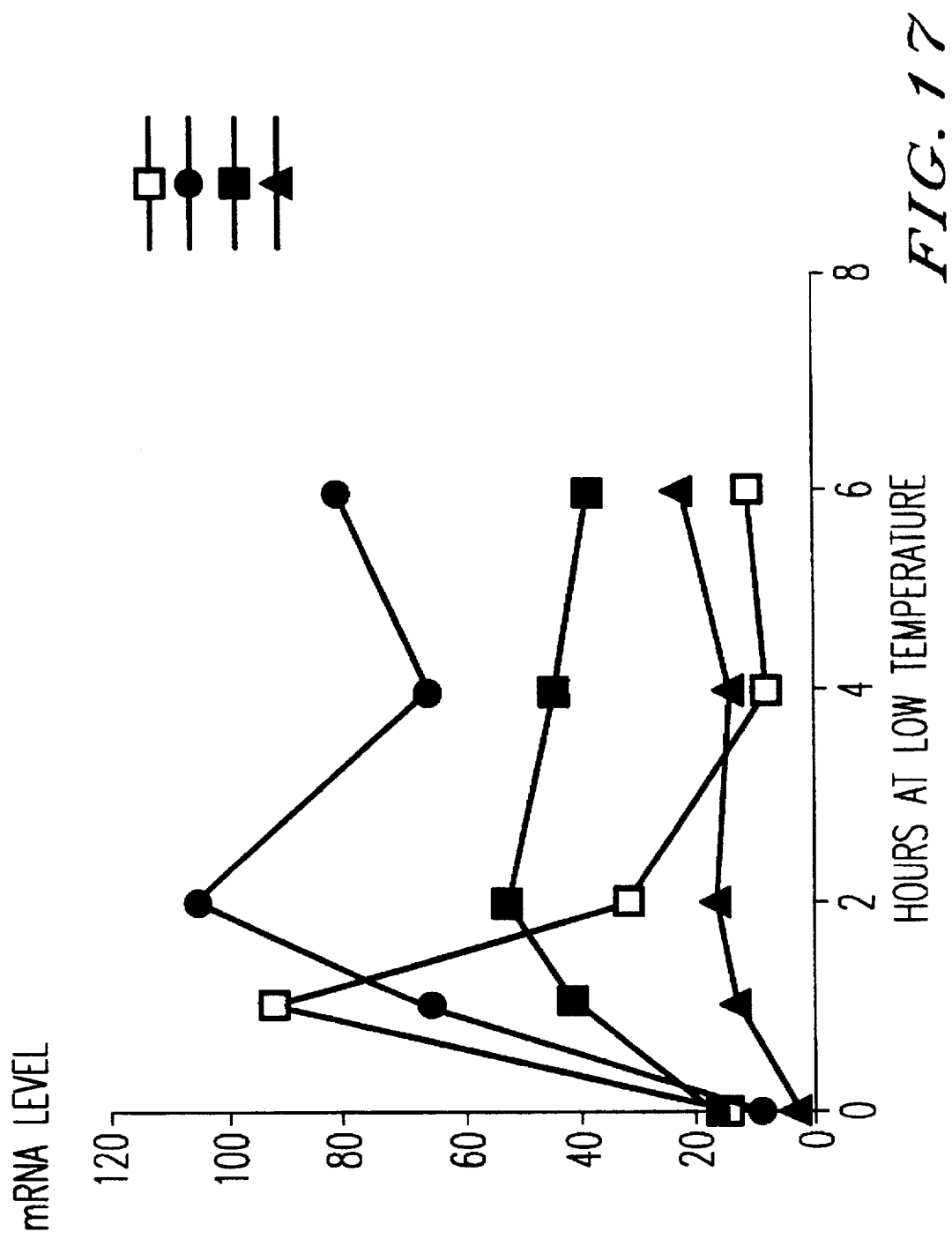
FIG. 17 depicts the expression of lacZ under the control of various cspA promoters at about 15°–16° C.: (□) endogenous cspA mRNA; (●) EL-lacZ mRNA; (■) M-lacZ mRNA; (▲) S-lacZ mRNA.

As can be seen in FIG. 17, the endogenous cspA mRNA (i.e., □) is present at high levels only one hour after transfer to the low temperature. In contrast, EL-lacZ (i.e., ●) and M-lacZ (i.e., ■) mRNAs are maintained at high levels for longer time periods. Only basal levels of S-lacZ (i.e., ▲) mRNA were observed at all temperatures.

These results confirm that the EL and M promoters may be used to drive gene expression at low temperatures, and that the increased expression from these promoters is reflected in an increased level of transcribed mRNA.

All of the references cited herein are hereby incorporated in their entireties by reference.

While this invention has been described with an emphasis upon a preferred embodiment, it will be obvious to those of ordinary skill in the art that variations in the preferred methods may be used, including variations due to improvements in the art, and that it is intended that the invention be practiced otherwise than as specifically described herein, to encompass these variations. Accordingly, this invention includes all modifications encompassed within the spirit and scope of the invention as defined by the following claims.

What is claimed is:

1. An expression vector comprising a gene operably linked to a DNA promoter having the nucleic acid sequence of SEQ ID NO:2, 3, 4, 5 or 6.

2. The vector of claim 1 wherein said promoter comprises the sequence of SEQ ID NO:2.

3. The vector of claim 1 wherein said promoter comprises the sequence of SEQ ID NO:3.

4. The vector of claim 1 wherein said promoter comprises the sequence of SEQ ID NO:4.

5. The vector of claim 1 wherein said promoter comprises the sequence of SEQ ID NO:5.

6. The vector of claim 1 wherein said promoter comprises the sequence of SEQ ID NO:6.

7. The vector of claim 1 which comprises λA01107 contained within the cell line of ATCC No. 75717.

8. The vector of claim 1 which comprises λPcspA contained within the cell line of ATCC No. 75718.

9. The vector of claim 1 which comprises plasmid pIK-M contained within the cell line of ATCC No. 75719.

10. The vector of claim 1 which comprises plasmid pIK-EL contained within the cell line of ATCC No. 76720.

11. An *E. coli* cell containing the vector of claim 2.
12. An *E. coli* cell containing the vector of claim 3.
13. An *E. coli* cell containing the vector of claim 4.
14. An *E. coli* cell containing the vector of claim 5.
15. An *E. coli* cell containing the vector of claim 6.
16. A nucleic acid comprising the vector of claim 2.
17. A nucleic acid comprising the vector of claim 3.
18. A nucleic acid comprising the vector of claim 4.
19. A nucleic acid comprising the vector of claim 5.
20. A nucleic acid comprising the vector of claim 6.
21. A vector comprising a pL promoter in which the −4 to +4 region shown in FIG. 1 (SEQ ID NO:1) has been mutated from GCACATCA to GGACAAGA.

22. A vector comprising a pL promoter in which the −10 region shown in FIG. 1 (SEQ ID NO:1) has been mutated from GATACT to TATAAT.

23. A vector comprising a pL promoter in which the −40 to −78 region shown in FIG. 1 (SEQ ID NO:1) has been deleted.

24. A vector comprising a pL promoter in which the −9 region shown in FIG. 1 (SEQ ID NO:1) has been mutated from GATACT to GATGCT.

25. A method of producing a protein, comprising the steps of:

transforming a host with a vector comprising a DNA promoter having the nucleic acid sequence of SEQ ID NO:2, 3, 4, 5 or 6 operably linked to a gene encoding a protein, culturing the host at about 37° C. for a time sufficient to allow an increase in culture density, and culturing the host at about 20° C. for a time sufficient to produce said protein.

26. The method of claim 25, wherein said protein is selected from the group consisting of viral proteins, insulin, interleukins, interferons and growth factors.

* * * * *

UNITED STATES PATENT AND TRADEMARK OFFICE
CERTIFICATE OF CORRECTION

PATENT NO. : 5,726,039
DATED : March 10, 1998
INVENTOR(S) : Amos B. OPPENHEIM, et al.

It is certified that error appears in the above-indentified patent and that said Letters Patent is hereby corrected as shown below:

On the title page, Item [*], the terminal disclaimer information, is missing. It should read:

--[*] The term of this patent shall not extend beyond the expiration date of Pat. No. 5,654,169.--

Signed and Sealed this

Nineteenth Day of May, 1998

Attest:

BRUCE LEHMAN

Attesting Officer

Commissioner of Patents and Trademarks